United States Patent [19]
Feng et al.

[11] Patent Number: 6,147,251
[45] Date of Patent: Nov. 14, 2000

[54] PROCESS FOR THE PREPARATION AND USES OF DERIVATIVES OF ESTERS OF α-METHYLENE-β-HYDROXY ACIDS

[75] Inventors: Xu Wu Feng, Bethany; Walter Nudenberg, Newtown, both of Conn.

[73] Assignee: Uniroyal Chemical Company, Inc., Middlebury, Conn.

[21] Appl. No.: 09/187,378

[22] Filed: Nov. 6, 1998

[51] Int. Cl.[7] .................................................. C07C 67/30
[52] U.S. Cl. ............................ 560/213; 549/206; 560/61; 560/62; 560/83; 560/212; 560/226; 562/599
[58] Field of Search ..................... 560/213, 212, 560/61, 62, 83, 226; 549/206; 562/599

[56] References Cited

U.S. PATENT DOCUMENTS

| | | | |
|---|---|---|---|
| 2,515,306 | 7/1950 | Ladd et al. | 260/487 |
| 3,260,708 | 7/1966 | Natta et al. | 260/79.5 |
| 3,743,669 | 7/1973 | Hillman et al. | 260/465.6 |
| 4,189,558 | 2/1980 | Witte et al. | 526/169.2 |
| 4,378,455 | 3/1983 | Kawasaki et al. | 526/114 |
| 5,527,951 | 6/1996 | Khan et al. | 560/219 |

OTHER PUBLICATIONS

Kimura et al., Polymer J., vol. 15, No. 4, pp. 293–301; 1983.
Benincasa et al., "Reductive Homo–Coupling of Methyl 2–Br–2–Cl–Carboxylates Promoted by CuBr–Fe," Tetrahedron Letters 36(7):1103–1106 (1995).
Hill, J. et al., "Functionalisation of the $\mu$ Position of Acrylate Systems By the Addition of Carbonyl Compounds: Highly Pressure–Dependent Reactions," Tetrahedron Letters 27(41):5007–5010 (1986).
Hoffmann et al., "Preparation of 2–(1–Hydroxyalkyl)acrylic Esters; Simple Three–Step Synthesis of Mikanecic Acid," Angew. Chem. Int. Ed. Engl. 22(10):795 (1983).
Rabe et al., "A New, efficient and Stereocontrolled Synthesis of Trisubstituted Alkenes via Functionalized Acrylic Esters," Angew. Chem. Int. Ed. Engl. 22(10):796–7 (1983).
Brown et al., "Organic Syntheses," 68:64 (1989).
J. Chem. Soc. Chem. Comm. 277–278 (1998).
McFadden et al. "Potential Inhibitors of Phosphoenolpyruvate Carboxylase II. Phosphonic Acid Substrate Analogues Derived from Reaction of Trialkyl Phosphites with Halometharcrylates" appearing in Australian Journal of Chemistry, at pages 301–314. Vol, 42 (1989).

*Primary Examiner*—James O. Wilson
*Assistant Examiner*—Robert W. Deemie
*Attorney, Agent, or Firm*—Raymond D. Thompson; Paul Grandinetti

[57] ABSTRACT

A process for the preparation of derivatives of halo-but-2-enoic acids and esters high in 2-ene content, several of which are novel. The esters and their derivatives are useful as promoters for the polymerization of ethylene or the copolymerization of ethylene with α-olefins and, optionally, nonconjugated polyenes. The promoters can also be combined with transition metal compounds, e.g., vanadium, to form combination promoter-catalyst compounds.

5 Claims, No Drawings

PROCESS FOR THE PREPARATION AND USES OF DERIVATIVES OF ESTERS OF α-METHYLENE-β-HYDROXY ACIDS

BACKGROUND OF THE INVENTION

1. Field of the Invention

The present invention is directed to a process for the preparation of derivatives of halo-but-2-enoic acids and esters high in 2-ene content and their use as catalyst promoters in ethylene polymerization and copolymerization, e.g., the preparation of a-olefin copolymers in which ethylene, at least one other higher a-olefin monomer, and, optionally, a non-conjugated diene, are copolymerized.

2. Description of Related Art

Polymerization of α-olefins to produce α-olefin copolymers and EPDM is well established in the art. In these polymerizations, a transition metal catalyst, most often a vanadium catalyst, and an organo-aluminum co-catalyst are added to a reaction mixture to catalyze the polymerization reaction. In order to enhance catalyst efficiency and/or regulate polymer molecular weight, a catalyst activator or promoter is frequently employed, providing the advantages of improved catalyst selectivity and efficiency including diene incorporation.

U.S. Pat. No. 2,515,306 discloses that if the hydrogenation of esters of 2,ω,ω,ω-tetrahalogenoalkanoic acid is carried out in neutral or acid media, i.e., while maintaining the reaction mixture at a pH of not over 7, the 2-halogen atom, i.e., the halogen on the carbon atom adjacent to the carboxyl group, is selectively removed without affecting the halogen atoms of the trihalogenomethyl group. By this method, compounds can be prepared that are useful in numerous syntheses involving reactions, such as, hydrolysis, hydrogenative coupling, dehydrohalogenation, and metathetical replacement.

U.S. Pat. No. 3,743,669 discloses that acrylates, acrylonitrile, acrylamides or vinyl ketones can be reacted, even at ambient temperature, with an aldehyde in the presence of an organic tertiary amine catalyst to produce the corresponding 2-(1-hydroxyalkyl)-acrylates, acrylonitriles, acrylamides or vinyl ketones in very good yields. These product monomers having an —OH moiety in their structure are said to exhibit, upon polymerization, good adhesive properties.

U.S. Pat. No. 5,527,951 discloses that tert-alkylmethoxy-substituted vanadium compounds are useful as catalysts for the polymerization of ethylene or the copolymerization of ethylene with a-olefins and (optionally) nonconjugated polyenes. It is preferred that the catalytic vanadium compound be used in combination with a promoter of a given structure, preferably one selected from the group consisting of butyl 4,4,4-trichlorobut-2-enoate, methyl 2-methyl-4,4,4-trichlorobut-2-enoate, ethyl 4,4,4-trichlorobut-2-enoate, 2-ethylhexyl 4,4,4-trichlorobut-2-enoate, and butyl perchlorocrotonate.

Hoffmann et al., *Angew. Chem. Int. Ed. Engl.* 22(10):795 (1983) reported that acrylate esters can be coupled readily at the a-position with a wide variety of aldehydes, also sensitive and functionalized representatives, in the presence of catalytic amounts of DABCO (1,4-diaza-bicyclo[2.2.2] octane) at room temperature.

Rabe et al., *Angew. Chem. Int. Ed. Engl.* 22(10):796–7 (1983) describe a reaction sequence that starts from inexpensive aldehydes and acrylic ester, and stereoselectively affords trisubstituted olefins.

Hill et al., *Tetrahedron Letters* 27 (41):5007–5010 (1986) disclose that aldehydes and ketones will add to acrylonitrile, acrylate esters, acrolein and α,β-enones with the formation of a range of 2(X)-propen-1-ols (X=CN, COOR, COR). The reactions are catalyzed by tertiary amines and are very sensitive to pressure. A wide variety of products may be obtained at pressures of 5 kbar or less, whereas most of the reactions do not occur at atmospheric pressure.

Benincasa et al., *Tetrahedron Letters* 36 (7):1103–1106 (1995) disclose that dimethyl 2,3-dialkyl-2,3-dichloro-butanedioates are efficiently prepared in dimethylformamide or dimethylsulfoxide, through reductive homo-coupling of methyl 2-to bromo-2-chlorocarboxylates promoted by CuBr—Fe.

Brown et al., *Organic Syntheses* 68:64 (1989) reported that homogeneous hydrogenation of the aldehyde-acrylate condensation products in the presence of organometallic catalysts give predominantly anti-isomers. The catalysts employed here are transitional-metal complexes consisting of complicated coordinating ligands. They also reported in *J. Chem. Soc. Chem. Comm.* 277–278 (1998) that such diastereoselectivity with these catalysts is observed when the a-hydroxy functional groups of the condensation products are silylated.

The foregoing are incorporated herein by reference in their entirety.

SUMMARY OF THE INVENTION

The present invention is directed to a process, based on non-ozone-depleting raw materials, for the preparation of derivatives of esters that are useful as catalyst promoters. More particularly, the present invention is directed to a process for the preparation of derivatives of esters of the formulae Ia or Ib:

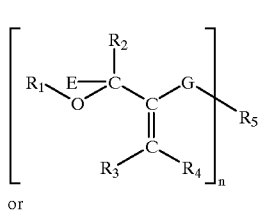

Ia or

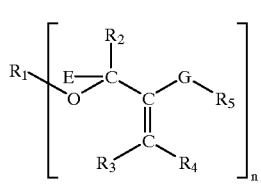

Ib wherein n is an integer of 1 to 4 that does not exceed the bonding capability of a given $R_1$ or $R_5$;

—E is

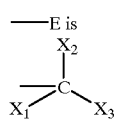

-continued

—G— is

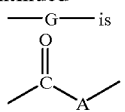

$X_1$, $X_2$, and $X_3$ are independently selected from the group consisting of halogen, alkyl, alkoxy, alkenyl, aryl, aryloxy, cyano, and hydrogen;

$R_1$ is selected from the group consisting of hydrogen, alkyl, alkaryl, aralkyl, haloalkyl, haloaryl, haloalkaryl, haloaralkyl, alkenyl, cycloalkyl, amino, xanthanyl, sulfinyl, sulfonyl, aryl, acyl, oxyalyl, and aroyl;

$R_2$ is selected from the group consisting of hydrogen, halogen, alkyl, alkoxy, alkenyl, aryloxy, cycloalkyl or —$COOR_6$ where $R_6$ is alkyl, alkenyl, cycloalkyl, aralkyl or aryl;

$R_3$ and $R_4$ are independently selected from the group consisting of hydrogen, halogen, hydroxy, alkyl, alkoxy, acyloxy, cycloalkyl, aryloxy, aralkyl, and aryl;

$R_5$ is selected from the group consisting of hydrogen, alkyl, alkaryl, aralkyl, haloalkyl, haloaryl, haloalkaryl, haloaralkyl, alkenyl, cycloalkyl, aryl, xanthanyl, sulfinyl, sulfonyl, aryl, acyl, oxyalyl, and aroyl; and A is selected from the group consisting of oxygen, sulfur, and $NR_7$ where $R_7$ is selected from the group consisting of hydrogen, alkyl, alkaryl, aralkyl, haloalkyl, haloaryl, haloalkaryl, haloaralkyl, alkenyl, cycloalkyl, and aryl;

wherein the process comprises reacting said ester with:

A) at least one Lewis acid or base and, optionally, a stoichiometric amount of mild hydride in the absence of a transition metal catalyst, or
B) hydrogen in the presence of a catalyst selected from the group consisting of transition metals or their oxides, or
C) at least one soluble catalyst selected from the group consisting of alkyl aluminums, alkyl hydrides, and soluble nickel or palladium salts.

In another aspect, the present invention is directed to an improvement in a process for the catalytic polymerization or copolymerization of ethylene wherein a promoter is employed, wherein the improvement comprises employing as the promoter at least one derivative of esters of the formulae Ia or Ib:

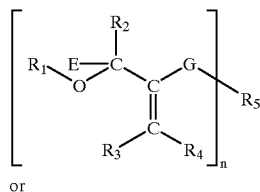

Ia or

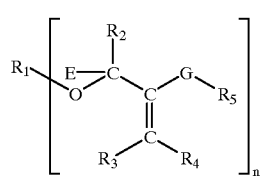

Ib wherein n is an integer of 1 to 4 that does not exceed the bonding capability of a given $R_1$ or $R_5$;

—E is

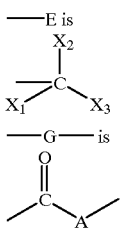

—G— is

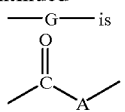

$X_1$, $X_2$, and $X_3$ are independently selected from the group consisting of halogen, alkyl, alkoxy, alkenyl, aryl, aryloxy, cyano, and hydrogen;

$R_1$ is selected from the group consisting of hydrogen, alkyl, alkaryl, aralkyl, haloalkyl, haloaryl, haloalkaryl, haloaralkyl, alkenyl, cycloalkyl, amino, xanthanyl, sulfinyl, sulfonyl, aryl, acyl, oxyalyl, and aroyl;

$R_2$ is selected from the group consisting of hydrogen, halogen, alkyl, alkoxy, alkenyl, aryloxy, cycloalkyl or —$COOR_6$ where $R_6$ is alkyl, alkenyl, cycloalkyl, aralkyl or aryl;

$R_3$ and $R_4$ are independently selected from the group consisting of hydrogen, halogen, hydroxy, alkyl, alkoxy, acyloxy, cycloalkyl, aryloxy, aralkyl, and aryl;

$R_5$ is selected from the group consisting of hydrogen, alkyl, alkaryl, aralkyl, haloalkyl, haloaryl, haloalkaryl, haloaralkyl, alkenyl, cycloalkyl, aryl, xanthanyl, sulfinyl, sulfonyl, aryl, acyl, oxyalyl, and aroyl; and A is selected from the group consisting of oxygen, sulfur, and $NR_7$ where $R_7$ is selected from the group consisting of hydrogen, alkyl, alkaryl, aralkyl, haloalkyl, haloaryl, haloalkaryl, haloaralkyl, alkenyl, cycloalkyl, and aryl;

wherein the derivative is synthesized by reacting said ester with:

A) at least one Lewis acid or base and, optionally, a stoichiometric amount of mild hydride in the absence of a transition metal catalyst, or
B) hydrogen in the presence of a catalyst selected from the group consisting of transition metals or their oxides, or
C) at least one soluble catalyst selected from the group consisting of alkyl aluminums, alkyl hydrides, and soluble nickel or palladium salts.

In still another aspect, the present invention is directed to a promoter-catalyst compound for the catalytic polymerization or copolymerization of ethylene having the structure $$M(O)_r X_m (\text{Promoter-minus H})_n$$

wherein:

M is a transition metal cation;
X is halide anion;
r is 0–3;
m is 0–6;
n is 1–7;
the maximum sum of r+m+n is 7; and Promoter is an ester of the structure

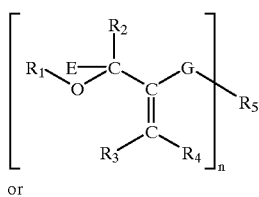

or

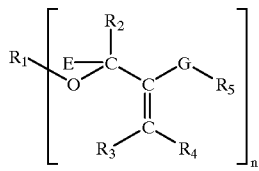

wherein
    n is an integer of 1 to 4 that does not exceed the bonding capability of a given $R_1$ or $R_5$;

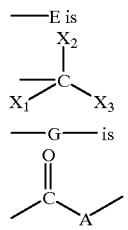

$X_1$, $X_2$, and $X_3$ are independently selected from the group consisting of halogen, alkyl, alkoxy, alkenyl, aryl, aryloxy, cyano, and hydrogen;

$R_1$ is selected from the group consisting of hydrogen, alkyl, alkaryl, aralkyl, haloalkyl, haloaryl, haloalkaryl, haloaralkyl, alkenyl, cycloalkyl, amino, xanthanyl, sulfinyl, sulfonyl, aryl, acyl, oxyalyl, and aroyl;

$R_2$ is selected from the group consisting of hydrogen, halogen, alkyl, alkoxy, alkenyl, aryloxy, cycloalkyl or —$COOR_6$ where $R_4$ is alkyl, alkenyl, cycloalkyl, aralkyl or aryl;

$R_3$ and $R_4$ are independently selected from the group consisting of hydrogen, to halogen, hydroxy, alkyl, alkoxy, acyloxy, cycloalkyl, aryloxy, aralkyl, and aryl;

$R_5$ is selected from the group consisting of hydrogen, alkyl, alkaryl, aralkyl, haloalkyl, haloaryl, haloalkaryl, haloaralkyl, alkenyl, cycloalkyl, aryl, xanthanyl, sulfinyl, sulfonyl, aryl, acyl, oxyalyl, and aroyl; and A is selected from the group consisting of oxygen, sulfur, and $NR_7$ where $R_7$ is selected from the group consisting of hydrogen, alkyl, alkaryl, aralkyl, haloalkyl, haloaryl, haloalkaryl, haloaralkyl, alkenyl, cycloalkyl, and aryl;

or an ester thereof prepared by a process comprising reacting said ester with:

A) at least one Lewis acid or base and, optionally, a stoichiometric amount of mild hydride in the absence of a transition metal catalyst, or B) hydrogen in the presence of a catalyst selected from the group consisting of transition metals or their oxides, or C) at least one soluble catalyst selected from the group consisting of alkyl aluminums, alkyl hydrides, and soluble nickel or palladium salts.

The ester starting materials can be prepared in high yield by the base catalyzed condensation of an aldehyde with an acrylate in the absence of solvents. Optionally, water can be present during the reaction to reduce the reaction cycle significantly.

Derivatives having chemical formulae IIa and IIb can be produced by reacting the ester starting materials with Lewis bases (nucleophilic) or Lewis acids (electrophilic) chemical reagents;

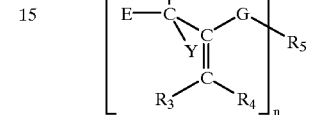

or

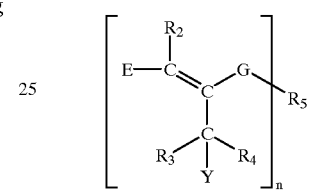

wherein n, E, G, $X_1$, $X^2$, $X^3$, $R^2$, $R^3$, $R^4$, $R^5$ and A are as described as above, and Y is selected from the group consisting of halogen, cyano, hydroxyl, hydrogen, alkyl, alkaryl, aralkyl, haloalkyl, haloaryl, haloalkaryl, haloaralkyl, alkenyl, cycloalkyl, xanthanyl, sulfinyl, sulfonyl, amino, aryl, acyloxy, oxyalyl, and aroyloxy.

These hydroxy esters, Ia, Ib, IIa and IIb, favorably acylated esters and most favorably acetylated esters, can undergo a hydrogenolysis reaction by a facile procedure using mild hydride reagents, such as sodium borohydride, in the absence of transition metal catalysts, to displace an acyloxy anion ($R^1$ is an acyl group and Y is acyloxy group) with a hydride anion at ambient temperature or by merely gently warming to produce the α,β-unsaturated esters of the formulae IIIa and IIIb in high yield. This hydrogenolysis selectively replaces the leaving group adjacent to the methylene-type unit to the exclusion of reduction reactions or other potential leaving groups.

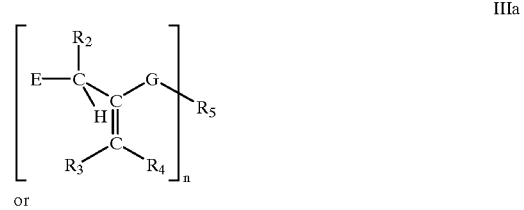

or

-continued

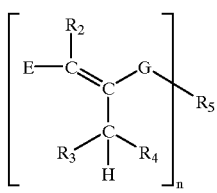

IIIb

The ester starting materials can also be hydrogenated with transition metal catalysts, such as palladium on charcoal, to yield a mixture of isomers having the structures of formulae IVa and IVb:

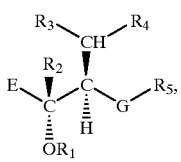

IVa antior

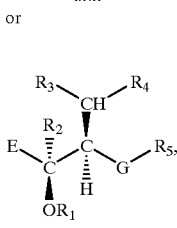

IVb syn-wherein

E, G, $X_1$, $X_2$, $X_3$, $R_1$, $R_2$, $R_3$, $R_4$, $R_5$, and A are as described as above.

The formation of the anti-product is favored over that of the syn-, the ratio of anti to syn being greater than 1:1 and as high as 22:1. Solvent choice has some impact on the anti/syn ratio. This stereoselective hydrogenation by a non-chiral catalyst provides a simple, practical method for making product preponderantly of the anti-isomer. When $X_1$, $X_2$, and $X_3$ are halogens, the hydrogenation converts the halogenated esters to the α-alkyl esters with no attack on the halogens or on the hydroxy (acyloxy or alkoxy) group.

These hydrogenated compounds of formulae IVa and IVb can be reacted with mild bases, such as, an alkyl metal bicarbonate, e.g., potassium bicarbonate, under gentle warming, to produce the α,β-unsaturated esters of the formulae IIIa and IIIb in high yield. The amount of base used for this reaction can be from catalytic to stoichiometric. For this elimination reaction, preferably $R_1$ in formulae IVa and IVb is selected from the group consisting of acyl, aroyl, oxyalyl, sulfonyl, and sulfinyl. Most preferably, $R_1$ is an acyl group.

DESCRIPTION OF THE PREFERRED EMBODIMENTS

As stated above, the present invention is directed to the preparation and uses of derivatives of esters of the formulae Ia and Ib:

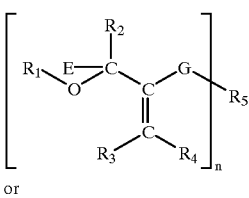

Ia or

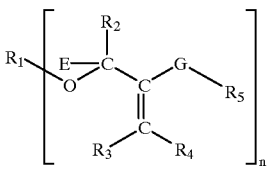

Ib wherein n is an integer of 1 to 4 that does not exceed the bonding capability of a given $R_1$ or $R_5$;

—E is

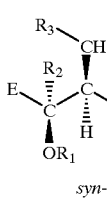

—G— is

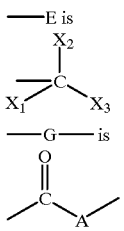

$X_1$, $X_2$, and $X_3$ are independently selected from the group consisting of halogen, alkyl, alkoxy, alkenyl, aryl, aryloxy, cyano, and hydrogen;

$R_1$ is selected from the group consisting of hydrogen, alkyl, alkaryl, aralkyl, haloalkyl, haloaryl, haloalkaryl, haloaralkyl, alkenyl, cycloalkyl, amino, xanthanyl, sulfinyl, sulfonyl, aryl, acyl, oxyalyl, and aroyl;

$R_2$ is selected from the group consisting of hydrogen, halogen, alkyl, alkoxy, alkenyl, aryloxy, cycloalkyl or —COOR$_6$ where $R_6$ is alkyl, alkenyl, cycloalkyl, aralkyl or aryl;

$R_3$ and $R_4$ are independently selected from the group consisting of hydrogen, halogen, hydroxy, alkyl, alkoxy, acyloxy, cycloalkyl, aryloxy, aralkyl, and aryl;

$R_5$ is selected from the group consisting of hydrogen, alkyl, alkaryl, aralkyl, haloalkyl, haloaryl, haloalkaryl, haloaralkyl, alkenyl, cycloalkyl, aryl, xanthanyl, sulfinyl, sulfonyl, aryl, acyl, oxyalyl, and aroyl; and A is selected from the group consisting of oxygen, sulfur, and NR$_7$ where R$_7$ is selected from the group consisting of hydrogen, alkyl, alkaryl, aralkyl, haloalkyl, haloaryl, haloalkaryl, haloaralkyl, alkenyl, cycloalkyl, and aryl;

wherein the process comprises reacting said ester with:

A) at least one Lewis acid or Lewis base and, optionally, a stoichiometric amount of mild hydride in the absence of a transition metal catalyst, or B) hydrogen in the presence of a catalyst selected from the group consisting of transition metals or their oxides, or C) at least one soluble catalyst selected from the group consisting of alkyl aluminums, alkyl hydrides, and soluble nickel or palladium salts.

Preferred examples of compounds of the structures Ia or Ib include butyl 2-methylene-3-hydroxy-4,4,4- trichlorobutyrate, butyl 2-methylene-3-acetoxy-4,4,4-trichlorobutyrate, and butyl 2-methylene-3-phenoxy-4,4,4-trichlorobutyrate.

Compounds with formulae Ia or Ib (where $R_1$ is H) can be made by a condensation reaction between an aldehyde and an acrylate. The so-called Hillman-Baylis reaction is well documented in the literature. More particularly, the compounds can be prepared by reacting an ester, a thioester, or an amide derivative of an α,β-olefinically unsaturated carboxylic acid with an aldehyde in the presence of a catalyst that is a tertiary amine, e.g., triethylene diamine, diazabicyclo-[2,2,2]-octane, pyrrocoline, quinuclidine, and other like sterically unhindered tertiary amines that are relatively strong bases.

Among the many acrylic monomers suitable for this reaction with an aldehyde, the following are representative, but are not intended to be limiting: methyl acrylate, ethyl acrylate, propyl acrylate, iso-octyl acrylate, 2-ethylhexyl acrylate, butyl acrylate, lauryl acrylate, phenyl acrylate, cyclohexylmethyl acrylate, cyclohexyl acrylate, cyclopentyl acrylate, phenylethyl acrylate, p-ethylphenyl acrylate, m-chlorophenyl acrylate, p-nitrophenyl acrylate, trichloromethyl acrylate, p-carboxymethylphenyl acrylate, m-methyoxyphenyl acrylate, furfuryl acrylates, and the like. Butyl acrylate is preferred for use in the practice of the present invention.

Typical aldehydes contemplated herein may be represented by the formula RCHO, wherein R includes substituted or unsubstituted, branched or straight-chain alkyl ($C_1$–$C_3$); substituted or unsubstituted, branched or straight-chain alkenyl ($C_1$–$C_9$); substituted or unsubstituted alk- ($C_1$–$C_4$) aryl; substituted or unsubstituted aralkyl ($C_1$–$C_4$); and substituted or unsubstituted aryl. The aryl moiety in the last three categories is typically phenyl.

Of the many aldehydes contemplated herein, the following are illustrative: to acetaldehyde, butyraldehyde, phenylacetaldehyde, benzaldehyde, octaldehyde, chloral, 2,2,2-tribromoacetaldehyde, crotonaldehyde, dibromoacetaldehyde, monobromoacetaldehyde, m-ethylphenylacetaldehyde, m-chlorobenzaldehyde, p-nitrophenylacetaldehyde, m-carbomethoxybenzaldehyde, p-methoxybenzaldehyde and the like.

The most preferred aldehyde for preparation of the esters employed in the practice of the present invention is chloral; however, it is also desirable to substitute hydrogen or an alkoxy group for one of the chlorine atoms of the chloral. If an alkoxy group is used, it will typically have from one to six carbon atoms, e.g., methoxy, ethoxy, propoxy, butoxy, pentoxy, hexoxy, or isomers thereof. Preferably, such an alkoxy group will have from one to four carbon atoms.

The reaction can be carried out over a wide range of temperatures. The reaction is effective at temperatures in the range of from about 0° C. to about 200° C., preferably in the range of from about 25° C. to about 125° C. If a solvent is used, the reaction is best carried out at a temperature at or below the boiling point of the solvent.

Although the reaction takes place quite readily at atmospheric pressure, superatmospheric or subatmospheric pressures may be employed. While batch processes can be used effectively, continuous or semi-continuous processes can also be used.

Insofar as the catalyst concentration is concerned, it is desirable that the catalyst be present in the range of from about 0.1 to about 20 percent by molar weight, based upon the total weight of the reactants, i.e., acrylic monomer and aldehyde. Preferably, the catalyst concentration is in the range of from about 1 to about 10 percent by molar weight.

More preferably, the catalyst concentration is in the range of from about 1 to about 5 percent by molar weight.

It is preferred that the reaction be carried out in the absence of any solvent, although water can optionally be present during the reaction to significantly reduce the reaction cycle. If desired, an inert solvent can be used, such as dioxane, tetrahydrofuran, acetonitrile, methyl ethyl ketone, dibutyl ether, chloroform, ethyl acetate, sulfolane, and the like.

It is preferred that these reaction products have the structure of formula Ia or Ib, wherein:

$X_1$ is selected from the group consisting of hydrogen, halogen, and alkoxy;

$X_2$ and $X_3$ are halogen;

$R_1$ is selected from the group consisting of hydrogen and acyl;

$R_2$ is selected from the group consisting of hydrogen, halogen, $C_1$–C6 alkyl, or —$COOR_6$ where $R_6$ is $C_1$–$C_{18}$ alkyl, $C_3$–$C_{18}$ alkenyl, $C_5$–$C_6$ cycloalkyl, $C_7$–$C_9$ aralkyl, and $C_6$–$C_{10}$ aryl;

$R_3$ and $R_4$ are independently selected from the group consisting of hydrogen and $C_1$–$C_{16}$ alkyl;

$R_5$ is selected from the group consisting of hydrogen, $C_1$–$C^{18}$ alkyl, $C_6$–$C_{10}$ aryl; $C_7$–$C_9$ alkaryl, $C_7$–$C_9$ aralkyl, $C_3$–$C_6$ alkenyl, $C_1$–$C_{18}$ haloalkyl, $C_6$–$C_{10}$ haloaryl, $C_7$–$C_9$ haloalkaryl, $C_7$–$C_9$ haloaralkyl; and A is oxygen.

It is more preferred that these reaction products have the structure of formulae Ia and Ib, wherein:

$X_1$, $X_2$ and $X_3$ are chlorine;

$R_1$ is selected from the group consisting of hydrogen and acetic acyl;

$R_2$ is selected from the group consisting of hydrogen, chlorine, $C_1$–$C_8$ alkyl, and —$COOR_6$ where $R_6$ is $C_1$–$C_8$ alkyl, benzyl, and phenyl;

$R_3$ and $R_4$ are independently selected from the group consisting of hydrogen and $C_1$–$C_7$ alkyl;

$R_5$ is selected from the group consisting of $C_1$–$C_{12}$ alkyl, phenyl, tolyl, benzyl, allyl, $C_1$–$C_2$ haloalkyl, and halophenyl; and A is oxygen.

In one aspect of the present invention, these compounds are used in the synthesis of compounds of the formulae IIa and IIb:

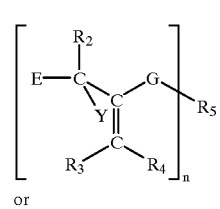

IIa or

-continued

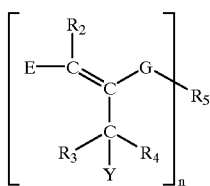
IIb wherein n, E, G, $X_1$, $X_2$, $X_3$, $R_2$, $R_3$, $R_4$, $R_5$, Y, and A are as described as above.

According to the present invention, the preparation of compounds of formulae IIa or IIb can be carried out by a rearrangement reaction of compounds of formulae Ia or Ib or facile procedures using nucleophilic and electrophilic reagents. The reagents include cyanides, amines, amides, alcohols, alkoxides, thiols, malonates, lithium alkyl aluminums, alkyl aluminums, alkyl lithiums, Grignard reagents, ammonium halides, metal halides, inorganic halides, alkylaluminoxanes, alkylaluminum oxides, alkylaluminum halides, hydrohalic acids, N-haloimides, halides of the elements in groups 13–17 in the periodic table, thionyl halides, sulfuryl halides, sulfonyl halides, oxylyl halides, acyl halides, acid anhydrides, and arenes.

Typical reagents for this preparation are, for example, water, lithium cyanide, sodium cyanide, potassium cyanide, propyl alcohol, isopropyl alcohol, ethanol, methanol, sodium methoxide, sodium ethoxide, potassium t-butoxide, phenol, thiophenol, ethylamine, propylamine, diethylamine, diisopropylamine, aniline, lithium diisopropylamide, diethyl malonate, dimethyl malonate, triethylaluminum, trimethylaluminum, methylaluminoxane, diisobutylaluminum oxide, methyl magnesium bromide, ethyl magnesium bromide, methyl lithium, pyridinium chloride, lithium chloride, lithium bromide, aluminum chloride, aluminum bromide, copper chloride, copper bromide, magnesium bromide, tin chloride, titanium chloride, diethylaluminum chloride, ethylaluminum sesquichloride, hydrochloric acid, hydrobromic acid, N-chlorosuccinimide, N-bromosuccinimide, phosphorus trichloride, phosphorus pentachloride, thionyl chloride, sulfuryl chloride, oxylyl chloride, acetyl chloride, acetic anhydride, methanesulfonyl chloride, benzene, and styrene.

The preferred reagents for this reaction are ethanol, isopropyl alcohol, phenol, methylaluminoxane, diisobutylaluminum oxide, phosphorus trichloride, phosphorus pentachloride, thionyl chloride, aluminum chloride, diethylaluminum chloride, ethylaluminum sesquichloride, hydrochloric acid, hydrobromic acid, acetic anhydride, acetyl chloride, and benzene.

It is preferred that these reaction products have the structure of formulae IIa and IIb,
wherein:

$X_1$ is selected from the group consisting of hydrogen, halogen, and alkoxy;

$X_2$ and $X_3$ are halogen;

Y is selected from the group consisting of hydrogen, halogen, $C_1$–$C_{16}$ alkyl, aryl, alkoxy, acyoxyl, and cyano;

$R_2$ is selected from the group consisting of hydrogen, halogen, $C_1$–$C_{16}$ alkyl, or —COOR$_6$ where $R_6$ is $C_1$–$C_{18}$ alkyl, $C_3$–$C_,$, alkenyl, $C_5$–$C_6$ cycloalkyl, $C_7$–$C_9$ arylalkyl or $C_6$–$C_{10}$ aryl;

$R_3$ and $R_4$ are independently selected from the group consisting of hydrogen, hydroxy, acyloxy, and $C_1$–$C_{16}$ alkyl;

$R_5$ is selected from the group consisting of hydrogen, $C_1$–$C_{18}$ alkyl, $C_6$–$C_{10}$ aryl; $C_7$–$C_9$ alkaryl, $C_7$–$C_9$ aralkyl, $C_3$–$C_6$ alkenyl, $C_1$–$C_{18}$ haloalkyl, $C_6$–$C_{10}$ haloaryl, $C_7$–$C_9$ haloalkaryl, $C_7$–$C_9$ haloaralkyl; and A is oxygen.

It is more preferred that these reaction products have a structure of formulae IIa or IIb,
wherein:

$X_1$, $X_2$, and $X_3$ are chlorine;

Y is selected from the group consisting of hydrogen, chlorine, bromine, and cyano;

$R_2$ is selected from the group consisting of hydrogen, chlorine, $C_1$–$C_8$ alkyl, and —COOR$_6$ where $R_6$ is $C_1$–$C_8$ alkyl, benzyl, and phenyl;

$R_3$ and $R_4$ are independently selected from the group consisting of hydrogen, hydroxyl, acyloxy, and $C_1$–$C_7$ alkyl;

$R_5$ is selected from the group consisting of $C_1$–$C_{12}$ alkyl, phenyl, tolyl, benzyl, allyl, $C_1$–$C_2$ haloalkyl, and halophenyl; and A is oxygen.

In another aspect of the present invention, these compounds of formulae Ia, Ib, IIa, and IIb are used in the synthesis of compounds of the formulae IIIa and IIIb:

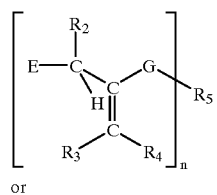
IIIa or

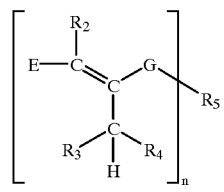
IIIb wherein E, G, $X_1$, $X_2$, $X_3$, $R_2$, $R_3$, $R_4$, $R_5$, and A are as defined above According to the present invention, this synthesis reaction is carried out by a facile procedure using mild hydride reagents, such as, alkali metal borohydrides, e.g., lithium, sodium, or potassium borohydride, in the absence of transition metal catalysts at ambient temperature or by gentle warming of the reaction mixture. In many cases, the reaction product is exclusively that shown in formula IIIb. This isomer is produced by displacement of the leaving group, $R_1O$— anion in formulae Ia and Ib, with a hydride anion, with concurrent allylic double bond rearrangement, to produce the α,β-unsaturated esters in high yield. The preferred leaving groups are those when $R_1$ is selected from the group consisting of acyl, aroyl, aryl, and sulfonyl. The most preferred leaving group is acyloxyl when $R_1$ is acyl.

This isomer can be produced from compounds of formulae IIa and IIb by mild hydrides. The preferred leaving groups are those when Y is selected from the group consisting of halide, aryloxide, thioaryloxide, and ammonium. The most preferred leaving group is a halide, for example, a chloride anion.

This hydrogenolysis selectively replaces the leaving group adjacent to the methylene unit to the exclusion of other potential leaving groups, such as, $X_1$, $X_2$, $X_3$, and —A—$R_5$.

The hydrogenolysis can be carried out with or without solvents. Representative solvents that can be used for this reaction include, but are not limited to, ethanol, isopropanol, butanol, t-butanol, dibutyl ether, diethyl ether, isopropyl ether, tetrahydrofuran, ethylene glycol, ethylene glycol butyl ether, ethylene glycol t-butyl ether, ethylene glycol t-butyl methyl ether, ethylene glycol diacetate, ethylene glycol dimethyl ether, ethylene glycol diethyl ether, di(ethylene glycol) dibutyl ether, di(ethylene glycol) diethyl ether, di(ethylene glycol) dimethyl ether, di(ethylene glycol) butyl ether, di(ethylene glycol) ethyl ether, di(ethylene glycol) methyl ether, poly(propylene glycol), poly(propylene glycol) monobutyl ether, poly(propylene glycol) diethyl ether, poly(propylene glycol) dimethyl ether, propylene carbonate, dipropyl carbonate, di(propylene glycol), di(propylene glycol) butyl ether, di(propylene glycol) methyl ether, di(propylene glycol) propyl ether, N,N-dimethyl formate, dimethyl sulfoxide, dioxanes, acetonitrile, toluene, xylene, hexane, heptane, pentane, cyclohexane, acetic acid, ethyl acetate, chloroform, methylene chloride, and the like.

Among the many mild hydrides that can be used in this hydrogenolysis reaction, the following are representative, but are not intended to be limiting: sodium borohydride, lithium borohydride, potassium borohydride, tetrabutylammonium borohydride, sodium borohydride-cesium chloride complex, sodium cyanoborohydride, sodium trimethoxyborohydride, sodium triacetoxyborohydride, lithium tributoxyborohydride, sodium acetoxyborohydride, zinc borohydride, zinc acetoxyborohydride, and the like. The preferred hydrides are lithium borohydride, sodium borohydride, and potassium borohydride. The most preferred hydride is sodium borohydride.

This hydrogenolysis reaction also can be carried out below ambient temperature. In this case, the hydrides used for the reaction include lithium aluminum hydride, aluminum hydride, lithium aluminum tri-t-butoxyhydride, lithium aluminum trimethoxyhydride, sodium aluminum dialkoxyhydride, diisobutyl aluminum hydride, lithium triethylborohydride, borane-tetrahydrofuran complex, borane-pyridine complex, borane-organic amine complex, borane-dimethyl sulfide complex, dichloroborane, dicyclohexyl borane, disulfidoborane, catecholborane, zinc borohydride-acetic acid complex, and the like. The preferred hydrides for use at these temperatures are diisobutyl aluminum hydride, lithium triethylborohydride, lithium aluminum tri-t-butoxyhydride, borane-tetrahydrofuran. The most preferred hydride is diisobutyl aluminum hydride.

This hydrogenolysis reaction can be carried out in the presence of phase transfer reagents/phase transfer catalysts to increase the reaction rate by the virtual increase of borohydride solubility in the reaction media. Such catalysts can be quaternary salts of group 15 elements in the Periodic Table; for instance, tetrabutylammonium acetate, tetrabutylammonium bromide, tetrabutylphosphonium bromide, and the like.

Some organic solvents can be also be used as phase transfer reagents for this hydrogenolysis, such as crown ethers, ethylene glycol, di(ethylene glycol), poly(propylene glycol), ethylene glycol ethers, di(ethylene glycol) ethers, poly(propylene glycol) ethers and the like.

It is preferred that these reaction products have the structure of formulae IIIa or IIIb, wherein:
$X_1$ is selected from the group consisting of hydrogen, halogen, and alkoxy;
$X_2$ and $X_3$ are halogen;
$R_2$ is selected from the group consisting of hydrogen, halogen, $C_1$–$C_{16}$ alkyl, and —$COOR_6$ where $R_6$ is $C_1$–$C_{18}$ alkyl, $C_3$–$C_{18}$ alkenyl, $C_5$–$C_6$ cycloalkyl, $C_7$–$C_9$ arylalkyl or $C_6$–$C_{10}$ aryl;
$R_3$ and $R_4$ are independently selected from the group consisting of hydrogen and $C_1$–$C_{16}$ alkyl;
$R_5$ is selected from the group consisting of hydrogen, $C_1$–$C_{18}$ alkyl, $C_6$–$C_{10}$ aryl; $C_7$–$C_9$ alkaryl, $C_7$–$C_9$ aralkyl, $C_3$–$C_6$ alkenyl, $C_1$–$C_{18}$ haloalkyl, $C_6$–$C_{10}$ haloaryl, $C_7$–$C_9$ haloalkaryl, and $C_7$–$C_9$ haloaralkyl; and
A is oxygen.

It is more preferred that these reaction products have the structure of formulae IIIa and IIIb, wherein:
$X_1$, $X_2$, and $X_3$ are chlorine;
$R_2$ is selected from the group consisting of hydrogen, chlorine, $C_1$–$C_8$ alkyl, and —$COOR_6$ where $R_6$ is $C_1$–$C_8$ alkyl, benzyl, or phenyl;
$R_3$ and $R_4$ are independently selected from the group consisting of hydrogen and $C_1$–$C_7$ alkyl;
$R_5$ is selected from the group consisting of $C_1$–$C_{12}$ alkyl, phenyl, tolyl, benzyl, allyl, $C_1$–$C_2$ haloalkyl, and halophenyl; and
A is oxygen.

U.S. Pat. No. 5,527,951 teaches that these α,β-unsaturated esters can be prepared by reacting a compound of the formula:

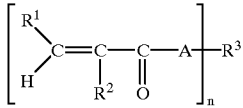

with a compound of the formula $C(X)(X^1)(X^2)(X^3)$ wherein X, $X^1$, $X^2$, and $X^3$ are all halogen, e.g., carbon tetrachloride, in the presence of a catalyst, such as, $RuCl_2[C_6H_5)_3]$, to produce a compound of the formula:

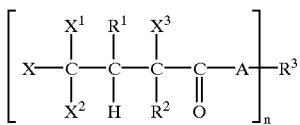

and dehydrohalogenating the compound, e.g., by treatment with an appropriate base. In these formulae:
n is 1, 2, 3, or 4;
X, $X^1$, and $X^2$ are halogen;
A is oxygen, sulfur, or halogen;
$R^1$ is hydrogen, halogen, $C_1$–$C_{16}$ alkyl, or —$COOR^4$ wherein $R^4$ is $C_1$–$C_{18}$ alkyl, $C_3$–$C_{18}$ alkenyl, $C_5$–$C_6$ cycloalkyl, $C_7$–$C_9$ aralkyl, or $C_6$–$C_{10}$ aryl;
$R^2$ is hydrogen, halogen, or $C_1$–$C_{16}$ alkyl;
with the provisos that:
when n is 1 and A is halogen, there is no. $R^3$;
when n is 1 and A is oxygen or sulfur, $R^3$ is hydrogen, $C_1$–$C_{18}$ alkyl, $C_6$–$C_{10}$ aryl, $C_7$–$C_9$ alkaryl, $C_7$–$C_9$ aralkyl, $C_3$–$C_6$ alkenyl, $C_1$–$C_1$, haloalkyl, $C_6$–$C_{10}$ haloaryl, $C_7$–$C_9$ haloalkaryl, or $C_7$–$C_9$ haloaralkyl;
when n is 2, A is oxygen or sulfur and $R^3$ is $C_2$–$C_{12}$ alkylene; and
when n is 3 or 4, A is oxygen or sulfur and $R^3$ is a $C_n$–$C_{12}$ alkyl radical having the valence n.

The process of the present invention is advantageous over this process in that it enables avoidance of the use of carbon tetrachloride, which is believed to contribute to atmospheric ozone depletion and also believed to be a health hazard for workers in this field, requiring the exercise of stringent safety precautions.

The unsaturated esters prepared by the above-described process may be used as adhesives, monomers for oil resistant polymers, organic oxidants for producing cationic metallocene catalysts, and promoters/oxidants/regulators for Z-N polymerization catalysts.

Of the many unsaturated esters that can be prepared by the process of the present invention, the following are preferred, particularly for their usefulness as promoters in the polymerization of ethylene or the copolymerization of ethylene with α-olefins and (optionally) nonconjugated polyenes: 2-methylene-3,4,4,4-tetrachlorobutyrates, 2-is methylene-3-bromo-4,4,4-trichlorobutyrates, 2-methylene-3-hydroxy-4,4,4-trichlorobutyrates, 2-methylene-3-acetoxy-4,4,4-trichlorobutyrates, 2-methylene-3-formoxy-4,4,4-trichlorobutyrates, 2-methylene-3-phenoxy-4,4,4-trichlorobutyrates, 2-methylene-3-ethoxy-4,4,4-trichlorobut-2-enoates, 2-methylene-3-methoxy-4,4,4-trichlorobutyrates, 2-methylene-3-isopropoxy-4,4,4-trichlorobutyrates, 2-methylene-3-ethoxy-4,4,4-trichlorobutyrates, 2-methylene-3-butoxy-4,4,4-trichlorobutyrates, 2-methylene-3-cyano-4,4,4-trichlorobutyrates, 2-chloromethyl-4,4,4-trichlorobut-2-enoates, 2-bromomethyl-4,4,4-trichlorobut-2-enoates, 2-hydroxymethyl-4,4,4-trichlorobut-2-enoates, 2-phenoxymethyl-4,4,4-trichlorobut-2-enoates, 2-acetoxymethyl-4,4,4 -trichlorobut-2-enoates, 2-formoxymethyl-4,4,4-trichlorobut-2-enoates, 2-methoxymethyl-4,4,4-trichlorobut-2-enoates, 2-ethoxymethyl-4,4,4-trichlorobut-2-enoates, 2-isopropoxymethyl-4,4,4-trichlorobut-2-enoates, 2-butoxymethyl-4,4,4-trichlorobut-2-enoates, 2-cyanomethyl-4,4,4-trichlorobut-2-enoates, 2-hydroxymethylene-4,4,4-trichlorobutyrates, 2-acetoxymethylene-4,4,4-trichlorobutyrates, 2-formoxymethylene-4,4,4-trichlorobutyrates, 2-chloromethylene-4,4,4-trichlorobutyrates, 2-bromomethylene-4,4,4-trichlorobutyrates, 2-cyanomethylene-4,4,4-trichlorobutyrates, 2-ethoxymethylene-4,4,4-trichlorobutyrates, 2-isopropoxymethylene-4,4,4-trichlorobutyrates, 2-butoxymethylene-4,4,4-trichlorobutyrates, 2-methylene-4,4,4-trichlorobutyrates, and 2-methyl-4,4,4-trichlorobut-2-enoates. Butyl esters of these illustrated samples are preferred. Butyl 2-methyl-4,4,4-trichlorobut-2-enoate, as disclosed in U.S. Pat. No. 5,527,951, is the most preferred.

It is well known in the art to use transition metal catalysts, most often vanadium compounds, as catalysts for the polymerization of ethylene or the copolymerization of is ethylene with α-olefins and (optionally) nonconjugated polyenes. For example, Natta et al. in U.S. Pat. No. 3,260,708 disclosed the use of a broad scope of vanadium compounds including vanadium halides, vanadium oxyhalides; vanadyl di- and triacetylacetonates and haloacetonates; vanadium tribenzoyl acetonates; vanadyl trialcoholates and haloalcoholates; the tetrahydrofuranates; the etherates; the aminates of vanadium tri- and tetrachloride and of vanadyl trichloride. Additionally, other useful catalysts of this type are disclosed in U.S. Pat. Nos. 4,189,558; 4,378,455; and 5,527,951, among others.

It is also well known to employ these catalysts in conjunction with cocatalysts, such as, for example, organo-lithium compounds and organo-aluminum compounds. Where an organo-aluminum compound is used, it is preferably an alkyl aluminum or an alkyl aluminum halide. Of the halide compounds, the chlorides are the most preferred. Among the preferred alkyl aluminum chlorides are ethyl aluminum sesquichloride, ethyl aluminum dichloride, diethyl aluminum chloride, and diisobutyl aluminum chloride.

In order to enhance catalyst efficiency and/or regulate polymer molecular weight, one or more catalyst activators or promoters are often used. The unsaturated esters prepared by the above described process or their derivatives with chemical formulae Ia, Ib, IIa, IIb, IIIa, and IIIb can be used as catalyst promoters in the polymerization of ethylene or the copolymerization of ethylene with α-olefins and (optionally) non-conjugated polyenes.

When a promoter compound, such as those prepared by the process of the present invention, is employed, the catalyst, cocatalyst, and catalyst promoter are preferably present in the polymerization reaction such that the molar ratio of cocatalyst to catalyst plus promoter is in the range of between about 0.5:1 and about 500:1. More preferably, this molar ratio is in the range of between about 1.5:1 and about 100:1. Most preferably, this molar ratio is in the range of between about 2.5:1 and about 10:1. The molar ratio of the catalyst promoter to the vanadium in the vanadium-containing compound is, preferably, in the range of between 1:1 and 100:1, more preferably, between 3:1 and 64:1, and most preferably, between 6:1 and 48:1.

The catalyst promoters can also be a composition of more than one compound of the formulae Ia, Ib, Ia, IIb, IIIa, and IIIb. The composition of these compounds as a catalyst promoter can be a completely random combination having any proportions.

When a promoter compound containing a hydroxy, or a xanthanyl, or an amino functional group, such as those prepared by the process of the present invention, is employed, the catalyst can be pre-mixed or reacted with the promoter to form a complex or a compound, for example to form a vanadate, to be used as a polymerization catalyst. This polymerization catalyst serves dual roles in polymerization both as a catalyst and as a catalyst promoter. This catalyst has a formula of V:

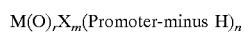

$$M(O)_rX_m(\text{Promoter-minus H})_n \qquad \qquad V$$

wherein:

M is a transition metal cation;

X is halide anion;

r is 0–3;

m is 0–6;

n is 1–7; and the sum of r+m+n is 7 in maximum.

Preferably, M is a transition metal cation selected from groups 3, 4, 5, 6, and 7 in the Periodic Table, and, more preferably, vanadium. X can be a chloride, bromide, or iodide anion, preferably a chloride and when m is greater than 1, X can additionally be a mixture of two or all three of these.

When this promoter-catalyst compound is used in polymerization, the cocatalyst and catalyst-catalyst promoter are preferably present in the polymerization reaction such that the molar ratio of cocatalyst to catalyst-promoter is in the range of between about 1:10 and about 500:1. More preferably, this molar ratio is in the range of between about 1:1 and about 100:1. Most preferably, this molar ratio is in the range of between about 3:1 and about 40:1.

The polymerization process is typically performed as follows. The catalyst composition, reaction medium, and co-monomers are introduced into the reaction vessel, which is typically composed of a non-reactive material, such as glass or stainless steel. In order to obtain best results, it is preferred that α-olefin (when employed) be anhydrous and thus it is preferable that such monomer be dried, e.g., by passing it through molecular sieves, prior to its introduction into the reactor. Preferably, the water content in the α-olefin should be no more that ten parts per million by weight.

Hydrogen gas may also be used to improve the regulation of the molecular weight of the polymer produced in the reaction. Specifically, lower molecular weights are obtainable when hydrogen gas is utilized.

In general, the catalyst concentration can range between about $1 \times 10^{-8}$ and about $3 \times 10^{-1}$ mole of vanadium per liter of total reaction medium (i.e., reaction medium plus monomer plus catalyst composition). Preferably, between about $1 \times 10^{-6}$ and about $5 \times 10^{-3}$ mole of vanadium per liter of total reaction medium is employed.

The polymerization reaction medium is typically an inert medium, such as, pentane, hexane, heptane, octane, isooctane, decane, benzene, toluene, and the like, although propylene monomer may serve as a reaction medium, optionally in combination with other liquid α-olefins.

The polymerization reaction occurs in the liquid state at a temperature in the range of between about −25° C. and about 70° C. More preferably, the temperature range of this reaction is between about −20° C. and about 50° C. Reaction time may vary from several minutes or less to several hours or more depending on factors such as reaction batch size, reaction temperature, the particular reactants selected, and other similar factors. If desired, the reaction may be monitored by sampling or reaction mixture solids measurement. Typically, the reaction time is in the range of from about 15 minutes to about 3 hours. Further, the reaction may be carried out in either a batch or a continuous manner.

Various features and aspects of the present invention are illustrated further in the examples that follow. While these examples are presented to show one skilled in the art how to operate within the scope of the invention, they are not intended in any way to serve as a limitation upon the scope of the invention.

EXAMPLES

Example 1

Preparation of Butyl 2-methylene-3-hydroxy-4,4,4-trichlorobutyrate

To a mixture of chloral (311.9 g) and butyl acrylate (208.8 g) charged in a 1 liter one-neck round bottom flask provided with a magnetic stir-bar was added DABCO (1,4-diazabicyclo[2,2,2]octane) (6.4 g). A milky solution resulted immediately after the DABCO addition. The reaction flask was provided with a reflux condenser and a thermometer. The temperature increased to 51° C. within 2 minutes and to 55° C. in twenty minutes. At this point, the solution turns clear yellow. One hour later, the temperature was at 71° C. and it started dropping slowly. Heat was provided to maintain the reaction temperature at 63° C. Six hours later, the unreacted materials were stripped off at 60–80° C./0.3 mm Hg. 375.8 g of yellow product oil was obtained, gas chromatography (GC) analysis showed the purity of this product to be 92%+ butyl 2-methylene-3-hydroxy-4,4,4-trichlorobutyrate. The product structure was confirmed by nuclear magnetic resonance (NMR) spectroscopy.

Example 2

Preparation of Butyl 2-methylene-3-acetoxy-4,4,4-trichlorobutyrate

To 1173.0 g of butyl 2-methylene-3-hydroxy-4,4,4-trichlorobutyrate (91% pure) charged in a 2-liter, 3-neck round bottom flask equipped with a mechanical stirrer, thermometer, and a condenser were added 520.0 g of acetic anhydride and 7.0 g of sodium acetate. The reaction mixture was heated at 120° C. for three hours. Unreacted acetic to anhydride and formed acetic acid were stripped off under vacuum at <80° C./0.6 mm Hg. After cooling to room temperature, the solid sodium acetate that had settled to the bottom of the flask was separated. 1236.1 g of acetylated product was obtained, 91.3% purity (GC analysis), 91.4% yield. The product structure was confirmed by NMR spectroscopy.

Example 3

Same as in Example 2, but without the use of sodium acetate in the acetylation process. A mixture of 193.9 g butyl 2-methylene-3-hydroxy-4,4,4-trichlorobutyrate (89% pure) and 75 g acetic anhydride was heated to reflux for three hours. When the reaction was finished, 205.3 g of product was obtained, 89% pure by GC analysis, 92% yield.

Example 4

Hydrogenation of Butyl 2-methylene-3-hydroxy-4,4,4-trichlorobutyrate and Butyl 2-methylene-3-acetoxy-4,4,4-trichlorobutyrate The hydrogenation reactions were performed in a Paar low pressure hydrogenator (Rocking type). Reaction materials, including catalyst, reactant and solvent, were charged into a heavy duty glass bottle. The bottle was mounted in the shaker inside a metal screen cage. Vacuum was applied to remove oxygen inside the bottle and replaced with hydrogen. The procedure was repeated three times to ensure complete oxygen removal. 20–30 psig of hydrogen was charged into the flask and the hydrogenator was turned on to operate. Hydrogen pressure inside the reactor was monitored and hydrogen was recharged, if necessary. After the hydrogen uptake stopped, hydrogen feed was cut off and the reaction mixture was removed from the reaction bottle. The product was obtained by filtering off catalyst and evaporating off solvent. The product was analyzed by GC and NMR to determine the reaction conversion and anti/syn ratio of the hydrogenated product.

Typical of the hydrogenation products (Table 1) and experimental examples is: 38.9 g of butyl 2-methylene-3-acetoxy-4,4,4-trichlorobutyrate was dissolved in a 55 ml of ethanol, to which 0.26 g of platinum oxide was added. 21 psi hydrogen was charged into the reaction bottle and the hydrogenation was monitored for the decrease in hydrogen pressure. Two and a half hours later, the reaction was stopped and the ethanol solvent was removed after recovering the platinum oxide catalyst. A yellow oil was obtained, 36.0 g of butyl 2-methyl-3-acetoxy-4,4,4-trichlorobutyrate, with a ratio of 12 anti-/syn-.

TABLE 1

Hydrogenation Results of butyl 2-methylene-3-hydroxy-4,4,4-trichlorobutyrate (A) and butyl 2-methylene-3-acetoxy-4,4,4-trichlorobutyrate (B)

| Example | Reactant | Catalyst and Solvent | Anti-:Syn-Ratio in the Product |
|---|---|---|---|
| 4a | A | $PtO_2$, Ethanol* | 5:1 |
| 4b | B | $PtO_2$, Ethanol* | 18:1 |
| 4c | B | $PtO_2$, Isopropanol | 10:1 |
| 4d | A | $PtO_2$, Ethanol | 1.4:1 |

TABLE 1-continued

Hydrogenation Results of butyl 2-methylene-3-hydroxy-4,4,4-
trichlorobutyrate (A) and butyl 2-methylene-3-acetoxy-
4,4,4-trichlorobutyrate (B)

| Example | Reactant | Catalyst and Solvent | Anti-:Syn-Ratio in the Product |
|---|---|---|---|
| 4e | B | $PtO_2$, Ethanol | 12:1 |
| 4f | A | $PtO_2$, Ethanol# | 3:1 |
| 4g | B | $PtO_2$, Ethanol# | 8.5:1 |
| 4h | butyl 2-methylene-3-propyloxy-4,4,4-trichlorobutyrate | $PtO_2$, Ethanol | 16.7:1 |

*1.5 wt % of sodium acetate was added to the reaction mixture.
The starting materials were washed with dilute hydrochloric acid solution.

Example 5

Preparation of butyl 2-methylene-3-phenoxy-4,4,4-trichlorobutyrate

Phenol (2.0 g) in 15 ml of tetrahydrofuran (THF) was slowly added to sodium hydride (1.0 g, 60% in oil) suspended in 5 ml THF at 0° C. Fifteen minutes later, 3.0 g of butyl 2-methylene-3-acetoxy-4,4,4-trichlorobutyrate (crude, GC: 86%) in 10 ml THF was slowly dropped into the phenoxide solution. The reaction was stirred at 0° C. for 3 hours and then permitted to warm to room temperature. The reaction was worked up by addition of 50 ml of water and 50 ml of ether. The organic layer was separated and the solvents were removed by vacuum. The resulting yellow oil was transferred to an alumina column and the product was eluted out with hexanes. A slightly yellow oil was obtained after removal of the hexanes, 3.1 g. The product was confirmed by NMR spectroscopy to be butyl 2-methylene-3-phenoxy-4,4,4-trichlorobutyrate.

Example 6

Preparation of Butyl 2-chloromethyl-4,4,4-trichlorobut-2-enoate

To 52.8 g of crude butyl 2-methylene-3-hydroxy-4,4,4-trichlorobutyrate was added 27.2 g thionyl chloride. The mixture was stirred at room temperature for three days. After removal of excess thionyl chloride, NMR indicated about one third of the starting material was converted into butyl 2-chloromethyl-4,4,4-trichlorobut-2-enoate. The product was dissolved in 100 ml of diethyl ether and washed with saturated potassium bicarbonate aqueous solution. 48.2 g of yellow product was obtained from the ether layer. NMR showed the product to be a mixture of butyl 2-chloromethyl-4,4,4-trichlorobut-2-enoate and To butyl 2-methylene-3-hydroxy-4,4,4-trichlorobutyrate. 8.5 g of a colorless oil as a 1:1 mixture of butyl 2-chloromethyl-4,4,4-trichlorobut-2-enoate and butyl 2-methylene-3-hydroxy-4,4,4-trichlorobutyrate was obtained by partial distillation of the crude thionyl chloride reaction product.

Example 7

Preparation of Butyl 2-methylene-3,4,4,4-tetrachlorobutyrate and Butyl 2-chloromethyl-4,4,4-trichlorobut-2-enoate To 24.4 g of crude butyl 2-methylene-3-hydroxy-4,4,4-trichlorobutyrate was added 13.2 g of excess thionyl chloride. The mixture was cooled to 7° C. in an ice bath and 2.0 g of triethylamine was very slowly dropped into the mixture. The reaction temperature rose to 30° C. and a dark colored solution was obtained. The mixture was stirred at room temperature overnight and then 20 ml of toluene was added to the mixture, followed by heating to reflux for 7 hours. When the reaction was finished, the mixture was very slowly poured into a potassium bicarbonate solution, followed by the addition of 50 ml of diethyl ether. The organic layer was separated and dried over magnesium sulfate. A dark colored oil was obtained after the solvent removal. The oil after elution through an alumina column with hexanes yielded a brown oil, 22.5 g. NMR showed it to be a mixture of butyl 2-chloromethyl-4,4,4-trichlorobut-2-enoate and butyl 2-methylene-3,4,4,4-tetrachlorobutyrate with a ratio of 73:27.

Example 8

Preparation of Butyl 2-methyl-4,4,4-trichlorobut-2-enoate 63.8 g of butyl 2-methyl-3-acetoxy-4,4,4-trichlorobutyrate (92%) containing butyl 2-methyl-3-hydroxy-4,4,4-trichlorobutyrate (2.6%) and butyl 2-methylene-3-acetoxy-4,4,4-trichlorobutyrate (3.5%) was charged to a flask equipped with a reflux condenser, magnetic stir bar, and a thermometer. 26.0 g of powder potassium bicarbonate, 2.8 g of sodium sarcosinate (40% aqueous solution) and 2.0 g of tetra-n-butylammonium bromide were is added to the flask. The reaction was heated up to 94° C. for three hours. GC analysis showed that the reaction mixture contains 60.5% butyl 2-methyl-4,4,4-trichlorobut-2-enoate and 4.2% butyl 2-methyl-2,4,4-trichlorobut-3-enoate along with rest of the starting material.

Example 9

Preparation of Butyl 2-methyl-4,4,4-trichlorobut-2-enoate 1236.1 g of crude 2-methylene-3-acetoxy-4,4,4-trichlorobutyrate (91.3%) containing about 2.5% 2-methylene-3-hydroxy-4,4,4-trichlorobutyrate and 747 ml of tetrahydrofuran was charged to a 2-liter flask equipped with a reflux condenser, magnetic stir bar, and a thermometer. 38.0 g of sodium borohydride was added in three portions to the stirred solution. The reaction temperature rose to 32° C. The reaction was heated slowly to 70° C. for three hours. NMR indicated 80% of the starting material was converted into product, butyl 2-methyl-4,4,4-trichlorobut-2-enoate. The reaction was heated for another six hours at 80° C. and the reaction was quenched by removal of tetrahydrofuran and addition of water. The organic layer was separated and GC analysis showed the presence of 79.2% butyl 2-methyl-4,4,4-trichlorobut-2-enoate, 1% butyl 2-methyl-2,4,4-trichlorobut-3-enoate, 6.6% unreacted starting material, butyl 2-methylene-3-acetoxy-4,4,4-trichlorobutyrate, 3% 1-o butyl 2-methyl-3-acetoxy-4,4,4-trichlorobutyrate, and 0.5% butyl 2-methylene-3-hydroxy-4,4,4-trichlorobutyrate. Hydrogenated product, butyl 2-methyl-3-acetoxy-4,4,4-trichlorobutyrate, was formed owing to the presence of water or traces of other protonic solvents in the reaction system.

The crude product can be purified by distillation. For instance, 123 g of this crude product was distilled at 0.06 mm Hg/65° C. Distilled product sampled from the pot, 84 g of distillate, by GC analysis showed an assay of the desired product, butyl 2-methyl-4,4,4-trichlorobut-2-enoate, of 93.8%.

Example 10

Preparation of Butyl 2-hydroxymethylene-4,4,4-trichlorobutyrate

This compound was obtained by a rearrangement reaction of butyl 2-methylene-3-hydroxy-4,4,4-trichlorobutyrate occurring at room temperature. An unpurified butyl 2-methylene-3-hydroxy-4,4,4-trichlorobutyrate product underwent the rearrangement reaction to form butyl 2-hydroxymethylene-4,4,4-trichlorobutyrate at a very slow rate—30% of the rearranged product was detected by NMR spectroscopy after four months at room temperature.

19.2 g of the product mixture was distilled at 93–95° C./mm Hg. 3.45 g of an oil of a slightly yellow color was obtained. NMR analysis showed it to be a mixture of butyl 2-hydroxymethylene-4,4,4-trichlorobutyrate and butyl 2-methylene-3-hydroxy-4,4,4-trichlorobutyrate in a 78:22 ratio.

Example 11

Preparation of Butyl 2-acetoxymethylene-4,4,4-trichlorobutyrate 0.5 g of the mixture of butyl 2-hydroxymethylene-4,4,4-trichlorobutyrate and butyl 2-methylene-3-hydroxy-4,4,4-trichlorobutyrate obtained from Example 10 was dissolved in 4 g of acetic anhydride. The reaction mixture was heated to reflux. After the reaction was completed, acetic acid and excess acetic anhydride were stripped off under vacuum. The crude product was dissolved in hexanes and filtered through an alumina column. 0.6 g of a yellow oil was obtained. NMR showed that the product was a mixture of butyl 2-acetoxymethylene-4,4,4-trichlorobutyrate and butyl 2-methylene-3-acetoxy-4,4,4-trichlorobutyrate in an 87:13 ratio.

Example 12

Preparation of EPDM Solution

Using the Butyl 2-methyl-4,4,4-trichlorobut-2-enoate of Example 9 A one gallon glass reactor equipped with temperature regulating coils was maintained at 30° C. and charged with 1.5 L of dry hexanes and 2.3 mmole of ethylaluminum sesquichloride in 1.8 ml of hexanes, and agitation was initiated. A 500 ml cylinder was pressurized with 4 psig of hydrogen, and the hydrogen was then charged to the reactor along with sufficient propylene to achieve a total pressure of 25 psig in the reactor. Ethylidene norbornene (ENB, 6 ml) was then added into the reactor. The reactor then was pressurized to 50 psig by a 1/1 molar ratio of ethylene and propylene. The gaseous ethylene/propylene mixture was fed continuously as required to maintain 50 psig pressure in the reactor throughout the polymerization. Vanadium oxytrichloride ($VOCl_3$, 0.16 mmole in 3.2 ml of hexanes) and butyl 2-methyl-4,4,4-trichlorobut-2-enoate (0.75 mmole in 1.5 ml of hexanes) were added into the reactor, followed by an additional 4 ml of ENB 5 minutes later. The temperature of the polymerization mixture rose to 34° C. briefly early in the polymerization process, and was cooled and maintained at 30° C. thereafter. After 0.5 hour, the polymerization was terminated by addition of isopropyl alcohol and the resultant polymer product was washed, separated from the polymerization mixture, and analyzed. Results of the analysis are listed in Table 2.

Example 13

Preparation of EPDM Solution Using Butyl 2-methylene-3-hydroxy-4,4,4-trichlorobutyrate A one gallon glass reactor equipped with temperature regulating coils was maintained at 30° C. and charged with 1.5 L of dry hexanes and 1.8 mmole of ethylaluminum sesquichloride in 1.4 ml of hexanes, and agitation was initiated. A 500 ml cylinder was pressurized with 20 psig of 10% hydrogen, and the hydrogen was then charged into the reactor along with sufficient propylene to achieve a total pressure of 25 psig in the reactor. Ethylidene norbornene (ENB, 5 ml) was then added into the reactor. The reactor then was pressurized to 50 psig with a 1/1 molar ratio of ethylene and propylene. The gaseous ethylene/propylene mixture was fed continuously as required to maintain a 50 psig pressure in the reactor throughout the polymerization. Vanadium oxytrichloride ($VOCl_3$, 0.2 mmole in 4.0 ml of hexanes) and distilled butyl 2-methylene-3-hydroxy-4,4,4-trichlorobutyrate (0.7 mmole in 1.4 ml of hexanes) were added to the reactor, followed by an additional 3 ml of ENB 5 minutes later. The temperature of the polymerization mixture rose to 36° C. briefly early in the polymerization process, and was cooled and maintained at 30° C. thereafter. After 20 minutes, the polymerization was terminated by addition of isopropyl alcohol and the resultant polymer product was washed, separated from the polymerization mixture and analyzed. Results of the analysis are listed in Table 2.

Example 14

Preparation of EPDM Solution Using Butyl 2-methylene-3-hydroxy-4,4,4-trichlorobutyrate The same procedure as described in Example 13 above was conducted except that crude butyl 2-methylene-3-hydroxy-4,4,4-trichlorobutyrate with 84% GC assay was used as the catalyst promoter. The properties of the produced polymer are presented in Table 2.

Example 15

Preparation of EPDM Solution Using Butyl 2-methylene-3-acetoxy-4,4,4-trichlorobutyrate The same procedure as described in Example 13 above was conducted except that crude butyl 2-methylene-3-acetoxy-4,4,4-trichlorobutyrate with 86% GC assay was used as the catalyst promoter. The properties of the produced polymer are presented in Table 2.

Example 16

Preparation of EPDM Solution Using Crude 2-methyl-4,4,4-trichlorobut-2-enoate The same procedure as described in Example 13 above was conducted except that crude butyl 2-methyl-4,4,4-trichlorobut-2-enoate containing a small amount of butyl 2-methylene-3-acetoxy-4,4,4-trichlorobutyrate was used as the catalyst promoter. The properties of the produced polymer are presented in Table 2.

Example 17

The same procedure as described in Example 13 above was conducted except that a mixture of butyl 2-methylene-3,4,4,4-tetrachlorobutyrate and butyl 2-chloromethyl-4,4,4-trichlorobut-2-enoate was used as catalyst promoter. Properties of the produced polymer was presented in Table 2.

Example 18

The same procedure as described in Example 13 above was conducted except that a mixture of butyl 2-methylene-3-hydroxy-4,4,4-tetrachlorobutyrate and butyl 2-chloromethyl-4,4,4-trichlorobut-2-enoate was used as the catalyst promoter. The properties of the produced polymer are presented in Table 2.

Example 19

The same procedure as described in Example 13 above was conducted except that a mixture of butyl 2-methyl-4,4,4-trichlorobut-2-enoate, butyl 2-methylene-3-acetoxy-4,4,4-trichlorobutyrate, butyl 2-methylene-3,4,4,4-tetrachlorobutyrate, and butyl 2-chloromethyl-4,4,4-trichlorobut-2-enoate was used as the catalyst promoter. The properties of the produced polymer are presented in Table 2.

Example 20

Preparation of EPDM Solution Using Butyl 2-methylene-3-phenoxy-4,4,4-trichlorobutyrate The same procedure as described in Example 13 above was conducted except that butyl 2-methylene-3-phenoxy-4,4,4-trichlorobutyrate was used as the catalyst promoter. The properties of the produced polymer are presented in Table 2.

Example 21

Preparation of EPDM Solution Using Butyl 2-hydroxymethylene-4,4,4-trichlorobutyrate The same procedure as described in Example 13 above was conducted except that the mixture of butyl 2-hydroxymethylene-4,4,4-trichlorobutyrate and butyl 2-methylene-3-hydroxy-4,4,4-trichlorobutyrate made in Example 10 was used as the catalyst promoter. The properties of the produced polymer are presented in Table 2.

Example 22

Preparation of EPDM Solution Using Butyl 2-acetoxymethylene-4,4,4-trichlorobutyrate The same procedure as described in Example 13 above was conducted except that the mixture of butyl 2-acetoxymethylene-4,4,4-trichlorobutyrate and butyl 2-methylene-3-acetoxy-4,4,4-trichlorobutyrate made in Example 11 was used as the catalyst promoter. The properties of the produced polymer are presented in Table 2.

Comparative Example

Preparation of EPDM Solution without Catalyst Promoter

A one gallon glass reactor equipped with temperature regulating coils was maintained at 30° C. and charged with 1.5 L of dry hexanes and 3.9 mmole of ethylaluminum sesquichloride in 3.0 ml of hexanes, and agitation was initiated. A 500 ml cylinder was pressurized with 40 psig of 10% hydrogen, and the hydrogen was then charged to the reactor along with sufficient propylene to achieve a total pressure of 25 psig in the reactor. Ethylidene norbornene (ENB, 10 ml) was then added to the reactor. The reactor then was pressurized to 50 psig with a 1/1 molar ratio of ethylene and propylene. The gaseous ethylene/propylene mixture was fed continuously as required to maintain a 50 psig pressure in the reactor throughout the polymerization. Vanadium oxytrichloride ($VOCl_3$, 1.0 mmole in 2.0 ml of hexanes) was added into the reactor, followed by an additional 4 ml of ENB 5 minutes later. The temperature of polymerization mixture rose to 37° C. briefly early in the polymerization process, and was cooled and maintained at 30° C. thereafter. After 20 minutes, the polymerization was terminated by addition of isopropyl alcohol and the resultant polymer product was washed, separated from the polymerization mixture and analyzed. Results of the analysis are listed in Tables 2 and 3.

TABLE 2

Polymerization Efficiency and Polymer Properties

| Example | Promoter | Catalyst Efficiency | Polymer E:P | ENB (wt. %) | $ML_{1+4}$ (@125° C.) | $M_w \times 10^{-5}$ | $M_w/M_n$ | $T_g$ (° C.) |
|---|---|---|---|---|---|---|---|---|
| 12 | A | 12914 | 59:41 | 7.6 | 36.0 | 3.12 | 2.30 | −49.9 |
| 13 | B | 6293 | 57:43 | 9.4 | 111.0 | 5.51 | 2.33 | −44.5 |
| 14 | C | 7379 | 55:45 | 8.7 | 94.0 | 4.94 | 2.35 | −46.5 |
| 15 | D | 7870 | 52:48 | 7.9 | 53.0 | 3.87 | 2.31 | −45.5 |
| 16 | E | 6690 | 53:47 | 8.6 | 52.0 | 3.93 | 2.15 | −45.4 |
| 17 | F | 7379 | 51:49 | 7.6 | 54.0 | 4.12 | 2.50 | −46.4 |
| 18 | G | 6394 | 54:46 | 8.8 | 61.0 | 4.11 | 2.44 | −45.0 |
| 19 | H | 6888 | 53:47 | 8.2 | 46.0 | 3.64 | 3.28 | −46.0 |
| 20 | I | 6189 | 54:46 | 8.8 | 62.0 | 4.16 | 2.24 | −45.8 |
| 21 | J | 3147 | 61:39 | 12.5 | 136 | 5.38 | 2.39 | −42.0 |
| 22 | K | 2596 | 62:38 | 11.9 | 119 | 4.66 | 2.24 | −42.4 |
| Comparative Example | none | 1377 | 65:35 | 18.2 | 146 | 6.51 | 3.79 | −37.0 |

A: Butyl 2-methyl-4,4,4-trichlorobut-2-enoate, 93.8% GC assay, made from this sodium borohydride process.
B: Butyl 2-methylene-3-hydroxy-4,4,4-trichlorobutyrate, distilled, 98.3% GC assay.
C: Butyl 2-methylene-3-hydroxy-4,4,4-trichlorobutyrate, 84% GC assay.
D: Butyl 2-methylene-3-acetoxy-4,4,4-trichlorobutyrate, 86% GC assay.
E: Crude 2-methyl-4,4,4-trichlorobut-2-enoate containing butyl 2-methylene-3-acetoxy-4,4,4-trichlorobutyrate in 83:17 ratio.
F: A mixture of butyl 2-methylene-3,4,4,4-tetrachlorobutyrate and butyl 2-chloromethyl-4,4,4-trichlorobut-2-enoate in 73:27 ratio.
G: A mixture of butyl 2-chloromethyl-4,4,4-trichlorobut-2-enoate and butyl 2-methylene-3-hydroxy-4,4,4-trichlorobutyrate in 1:1 ratio.
H: A mixture of E and F (1:1).
I: Butyl 2-methylene-3-phenoxy-4,4,4-trichlorobutyrate.

TABLE 2-continued

Polymerization Efficiency and Polymer Properties

| Example | Promoter | Catalyst Efficiency | Polymer E:P | ENB (wt. %) | $ML_{1+4}$ (@125° C.) | $M_w \times 10^{-5}$ | $M_w/M_n$ | $T_g$(° C.) |
|---|---|---|---|---|---|---|---|---|

J: A mixture of butyl 2-hydroxymethylene-4,4,4-trichlorobutyrate and butyl 2-methylene-3-hydroxy-4,4,4-trichlorobutyrate in 78:22 ratio.
K: A mixture of butyl 2-acetoxymethylene-4,4,4-trichlorobutyrate and butyl 2-methylene-3-acetoxy-4,4,4-trichlorobutyrate in 87:13 ratio.

Catalyst efficiency is presented in terms of pounds of polymer/pound of vanadium.

Weight average molecular weight ($M_w$), number average molecular weight ($M_n$) and $M_w/M_n$ were measured in orthodichlorobenzene at 130° C. on a Waters $GPC_{150}$° C. gel permeation chromatograph equipped with a Waters RA401 refractive index detector and Waters Styragel HT column (10E6 Å, 10E5 Å, 10E4 A, 10E3 Å). Molecular weights were calculated from elution times calibrated against polystyrene standards from American Polymer Standards Corp. (narrow molecular weight distribution, $M_n$ from 9300 to $2.1 \times 10^6$).

Mooney Viscosity ($ML_{1+4}$@125° C.) of the polymer products was determined on a -1-0 Monsanto Mooney Viscometer model MV 2000 according to ASTM standard D1646.

Ethylene, propylene, and ENB composition of the polymer products was determined by infrared spectroscopy of thin polymer films in a Perkin-Elmer infrared spectrophotometer model Paragon 1000PC, according to ASTM standard 3900.

Glass transition temperature ($T_g$) was measured by differential scanning calorimetry upon 20–25 mg of polymer sample molded at 150° C. for 15 minutes followed by annealing at room temperature for 24 hours. $T_g$ is reported as the midpoint of the glass transition on the heating curve of the sample, recorded on a Perkin-Elmer $DSC_7$ differential scanning calorimeter (from −100° C. to 180° C. at a heating rate of 20° C./minute).

Example 23

Preparation of EPDM Solution Using Bis(2-butoxycarbonyl-4,4,4-trichlorobuten-3-oxy) Chlorovanadium Oxide {O=VCl[O—CH($CCl_3$)C(=$CH_2$)$CO_2C_4H_9$]$_2$}

The vandate catalyst was prepared by mixing $VOCl_3$ with a required amount of butyl 2-methylene-3-hydroxy-4,4,4-trichlorobutyrate (distilled, 98.3% assay) in hexane solution. It was purged with Argon gas to remove hydrogen chloride after mixing.

A one gallon glass reactor equipped with temperature regulating coils was maintained at 30° C. and charged with 1.5 L of dry hexanes and 1.8 mmole of ethylaluminum sesquichloride in 1.4 ml of hexanes, and agitation was initiated. A 500 ml cylinder was pressurized with 20 psig of 10% hydrogen, and the hydrogen was then charged to the reactor along with sufficient propylene to achieve a total pressure of 25 psig in the reactor. Ethylidene norbornene (ENB, 10 ml) was then added to the reactor. The reactor then was pressurized to 50 psig with a 1/1 molar ratio of ethylene and propylene. The gaseous ethylene/propylene mixture was fed continuously as required to maintain a 50 psig pressure in the reactor throughout the polymerization. 0.14 mmole of O=VCl[O—CH($CCl_3$)C(=$CH_2$)$CO_2C_4H_9$]$_2$ in 1.5 ml hexanes was added to the reactor, followed by an additional 4 ml of ENB 5 minutes later. The temperature of polymerization mixture rose to 37° C. briefly early in the polymerization process, and was cooled and maintained at 30° C. thereafter. After 20 minutes, the polymerization was terminated by addition of isopropyl alcohol and the resultant polymer product was washed, separated from the polymerization mixture and analyzed. Results of the analysis are listed in Table 3.

Example 24

Preparation of EPDM Solution Using Tris(2-butoxycarbonyl-4,4,4-trichlorobuten-3-oxy) vanadium Oxide {O=V[O—CH($CCl_3$)C(=$CH_2$) $CO_2C_4H_9$]$_3$}

The same procedure as described in Example 23 above was conducted except that the vanadate, tris(2-butoxycarbonyl-4,4,4-trichlorobuten-3-oxy)vanadium oxide, was used as the catalyst. The properties of the produced polymer are presented in Table 3.

TABLE 3

Polymerization Efficiency and Polymer Properties in Vanadate Polymerization

| Example | Catalyst | Catalyst Efficiency | Polymer E:P | ENB (wt. %) | $ML_{1+4}$ | $M_w \times 10^{-5}$ | $M_w/M_n$ | $T_g$(° C.) |
|---|---|---|---|---|---|---|---|---|
| 23 | O=VCl[O—CH($CCl_3$)C($CH_2$)$CO_2C_4H_9$]$_2$ | 8184 | 67:33 | 19.6 | 169 @ 100° C. | 7.14 | 2.56 | −35.4 |
| 24 | O=V[O—CH($CCl_3$)C($CH_2$)$CO_2C_4H_9$]$_3$ | 10233 | 66:34 | 16.3 | 145.0 @ 125° C. | 7.41 | 2.42 | −38.8 |
| Comparative Example | $VOCl_3$ | 1377 | 65:35 | 18.2 | 146.0 @ 125° C. | 6.51 | 3.79 | −37.0 |

In view of the many changes and modifications that can be made without departing from principles underlying the invention, reference should be made to the appended claims for an understanding of the scope of the protection to be afforded the invention.

What is claimed is:

1. A process for the preparation of compounds of the formula:

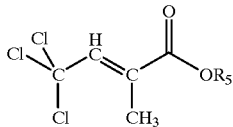

from an ester of the formula:

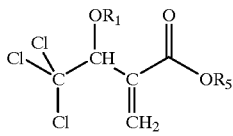

wherein

R$_1$ is selected from the group consisting of hydrogen, alkyl, alkaryl, aralkyl, haloalkyl, haloaryl, haloalkaryl, haloaralkyl, alkenyl, cycloalkyl, amino, xanthanyl, sulfinyl, sulfonyl, aryl, acyl, oxyalyl, and aroyl; and R$_5$ is selected from the group consisting of hydrogen, alkyl, alkaryl, aralkyl, haloalkyl, haloaryl, haloalkaryl, haloaralkyl, alkenyl, cycloalkyl, aryl, xanthanyl, sulfinyl, sulfonyl, aryl, acyl, oxyalyl, and aroyl;

wherein the process comprises reacting said ester with:

A) at least one Lewis acid or base and, optionally, a stoichiometric amount of mild hydride in the absence of a transition metal catalyst, or B) hydrogen in the presence of a catalyst selected from the group consisting of transition metals or their oxides to form at least one intermediate and then reacting said at least one intermediate with a mild base in a catalytic to stoichiometric amount.

2. The process of claim 1 comprising reacting said ester with at least one Lewis acid or base and, optionally, a stoichiometric amount of mild hydride in the absence of a transition metal catalyst.

3. The process of claim 2 wherein the Lewis acid or base is selected from the group consisting of cyanides, amines, amides, alcohols, alkoxides, thiols, malonates, lithium alkyl aluminums, alkyl aluminums, alkyl lithiums, Grignard reagents, ammonium halides, metal halides, inorganic halides, alkylaluminum oxides, alkylaluminum halides, hydrohalic acids, N-haloimides, halides of the elements in groups 13–17 in the periodic table, thionyl halides, sulfuryl halides, sulfonyl halides, oxylyl halides, acyl halides, acid anhydrides, and arenes.

4. The process of claim 2 wherein the mild hydride is selected from the group consisting of sodium borohydride, lithium borohydride, potassium borohydride, tetrabutylammonium borohydride, sodium borohydride-cesium chloride complex, sodium cyanoborohydride, sodium trimethoxyborohydride, sodium triacetoxyborohydride, lithium tributoxyborohydride, sodium acetoxyborohydride, zinc borohydride, and zinc acetoxyborohydride.

5. The process of claim 1 wherein said at least one intermediate is a mixture of derivatives of the structure:

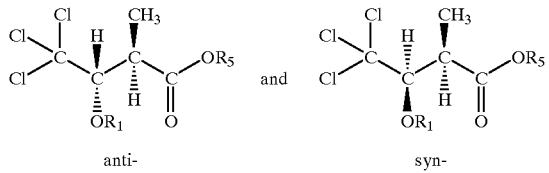

wherein the ratio of anti- to syn- is greater that 1:1.

* * * * *